US00PP22259P2

(12) United States Plant Patent
Kolster et al.

(10) Patent No.: US PP22,259 P2
(45) Date of Patent: Nov. 22, 2011

(54) ***HYDRANGEA* PLANT NAMED 'HOKOMAC'**

(50) Latin Name: *Hydrangea macrophylla*
Varietal Denomination: Hokomac

(75) Inventors: Peter R. Kolster, Boskoop (NL); Cornelis P. Eveleens, De Kwakel (NL)

(73) Assignee: Kolster Beheer B.V., Boskoop (NL)

( * ) Notice: Subject to any disclaimer, the term of this patent is extended or adjusted under 35 U.S.C. 154(b) by 111 days.

(21) Appl. No.: 12/658,051

(22) Filed: Feb. 1, 2010

(51) Int. Cl.
*A01H 5/00* (2006.01)

(52) U.S. Cl. ..... Plt./250

(58) Field of Classification Search ..... Plt./250
See application file for complete search history.

(56) References Cited

U.S. PATENT DOCUMENTS

PP18,823 P2 * 5/2008 Klaveren ..... Plt./250

OTHER PUBLICATIONS

UPOV ROM GTITM Computer Database, GTI Jouve Retrieval Software 2011/01 Citation for 'Hokomac'.*

Anonymous. "Hydrangea macrophylla 'Hokomac' Everlasting Coral PPAF" Plants Nouveau. Available at: http://plantsnouveau.com/ Accessed Jul. 14, 2011.*

* cited by examiner

*Primary Examiner* — Wendy C Haas
(74) *Attorney, Agent, or Firm* — C. A. Whealy

(57) ABSTRACT

A new and distinct cultivar of *Hydrangea* plant named 'Hokomac', characterized by its narrowly upright plant habit; strong erect stems; relatively small leaves; and mophead-type inflorescences with red purple and green-colored flowers.

2 Drawing Sheets

Botanical designation: *Hydrangea macrophylla.*
Cultivar denomination: 'HOKOMAC'.

CROSS-REFERENCED TO RELATED APPLICATIONS

Title: *Hydrangea* Plant Named 'Hokomarevo' (U.S. Plant patent application Ser. No. 12/658,049).
Title: *Hydrangea* Plant Named 'Hokomathyst' (U.S. Plant patent application Ser. No. 12/658,050).

BACKGROUND OF THE INVENTION

The present invention relates to a new and distinct cultivar of *Hydrangea* plant, botanically known as *Hydrangea macrophylla* and hereinafter referred to by the name 'Hokomac'.

The new *Hydrangea* plant is a naturally-occurring whole plant mutation of *Hydrangea macrophylla* 'Xian', not patented. The new *Hydrangea* plant was discovered and selected by the Inventors as a single flowering plant from within a population of plants of 'Xian' in a controlled greenhouse environment in Boskoop, The Netherlands in July, 2006.

Asexual reproduction of the new *Hydrangea* plant by vegetative cuttings in a controlled greenhouse environment in Boskoop, The Netherlands since August, 2006, has shown that the unique features of this new *Hydrangea* plant are stable and reproduced true to type in successive generations.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Hokomac'. These characteristics in combination distinguish 'Hokomac' as a new and distinct cultivar of *Hydrangea* plant:

1. Narrowly upright plant habit.
2. Strong erect stems.
3. Relatively small leaves.
4. Mophead-type inflorescences with red purple and green-colored flowers.

Plants of the new *Hydrangea* differ from plants of the parent, 'Xian', in the following characteristics:

1. Plants of the new *Hydrangea* are more freely flowering than plants of 'Xian'.
2. Sterile flowers of the new *Hydrangea* have smaller sepals than sterile flowers of plants of 'Xian'.
3. Plants of the new *Hydrangea* and 'Xian' differ in flower color.

Plants of the new *Hydrangea* differ from plants of the *Hydrangeas* 'Hokomarevo' (U.S. Plant patent application Ser. No. 12/658,049) and 'Hokomathyst' (U.S. Plant patent application Ser. No. 12/658,050) primarily in flower color.

Plants of the new *Hydrangea* can also be compared to plants of *Hydrangea* 'Magical Diamond', not patented. Plants of the new *Hydrangea* differ primarily from plants of 'Magical Diamond' in the following characteristics:

1. Plants of the new *Hydrangea* are more upright than plants of 'Magical Diamond'.
2. Plants of the new *Hydrangea* have stronger stems than plants of 'Magical Diamond'.
3. Inflorescences of plants of the new *Hydrangea* are flatter than and not as globular as inflorescences of plants of 'Magical Diamond'.
4. Sterile flowers of plants of the new *Hydrangea* have smaller, thicker and more durable sepals than sterile flowers of plants of 'Magical Diamond'.

BRIEF DESCRIPTION OF THE PHOTOGRAPHS

The accompanying colored photographs illustrate the unique appearance of the new *Hydrangea* plant, showing the colors as true as it is reasonably possible to obtain in colored reproductions of this type. Colors in the photographs may differ from the color value cited in the detailed botanical description which accurately describe the colors of the new *Hydrangea* plant.

The photograph on the first sheet comprises a side perspective view of a typical plant of 'Hokomac' grown in a container.

The photograph at the top of the second sheet is a close-up view of a typical inflorescence of 'Hokomac'.

The photograph at the bottom of the second sheet is a close-up view of typical leaf of 'Hokomac'.

DETAILED BOTANICAL DESCRIPTION

Plants used in the aforementioned photographs and in the following description were grown in two-liter containers during the late spring in a shaded glass-covered greenhouse in Boskoop, The Netherlands under conditions which closely approximate commercial production conditions. During the production of the plants, day and night temperatures ranged from 17° C. to 19° C. Plants of the new *Hydrangea* were two years old when the photographs and description were taken. In the following description, color references are made to The Royal Horticultural Society Colour Chart, 2001 Edition, except where general terms of ordinary dictionary significance are used.

Botanical description: *Hydrangea macrophylla* 'Hokomac'.

Parentage: Naturally-occurring whole plant mutation of *Hydrangea macrophylla* 'Xian', not patented.

Propagation:

- *Method.*—By softwood cuttings.
- *Time to initiate roots, summer.*—About three weeks at temperatures of 15° C. to 25° C.
- *Time to initiate roots, winter.*—About five weeks at temperatures of 10° C. to 20° C.
- *Time to produce a rooted young plant, summer.*—About six weeks at temperatures of 15° C. to 25° C.
- *Time to produce a rooted young plant, winter.*—About ten weeks at temperatures of 10° C. to 20° C.
- *Root description.*—Medium in thickness, fibrous; creamy white in color.
- *Rooting habit.*—Moderately branching; medium in density.

Plant description:

- *Form/growth habit.*—Upright plant habit; narrow inverted triangle; strong erect stems; about ten lateral branches develop per plant, pinching enhances lateral branch development; moderately vigorous growth habit.
- *Plant height.*—About 53.8 cm.
- *Plant diameter or area of spread.*—About 47.3 cm.
- *Lateral branches.*—Length: About 23.6 cm. Diameter: About 6 mm. Internode length: About 7.1 cm. Texture, developing and fully developed: Smooth, glabrous. Angle: Mostly erect. Strength: Strong. Color, developing: Close to 144A. Color, fully developed: Between 199A and N199C.

Foliage description:

- *Arrangement.*—Opposite simple.
- *Length.*—About 10.1 cm.
- *Width.*—About 8.5 cm.
- *Shape.*—Broadly ovate.
- *Apex.*—Acute.
- *Base.*—Rounded to attenuate.
- *Margin.*—Serrate.
- *Texture, upper and lower surfaces.*—Smooth, glabrous.
- *Venation pattern.*—Pinnate.
- *Color.*—Developing leaves, upper surface: Between 139A and 141A. Developing leaves, lower surface: Between 137C and 138B. Fully expanded leaves, upper surface: Close to 137A; venation, close to 145C. Fully expanded leaves, lower surface: Close to 138B; venation, close to 145B.
- *Petiole.*—Length: About 3 cm. Diameter: About 4 mm. Texture, upper and lower surfaces: Smooth, glabrous. Color, upper and lower surfaces: Close to 144C.

Flower description:

- *Flower type and habit.*—Single fertile and sterile flowers arranged on terminal mophead-type panicles; panicles flattened globular; sterile flowers face upright to outwardly and fertile flowers face upright.
- *Fragrance.*—None detected.
- *Natural flowering season.*—Continuous flowering from late spring to late summer in The Netherlands.
- *Flower longevity.*—Sterile flowers last about four weeks on the plant; sterile flowers persistent.
- *Quantity of flowers.*—Freely flowering habit; about 70 fertile flowers and about 130 sterile flowers per panicle.
- *Panicle height.*—About 7.1 cm.
- *Panicle diameter.*—About 12.1 cm.
- *Flower buds.*—Length: About 2 mm. Diameter: About 2.5 mm. Shape: Flattened globular. Color: Close to 73B.
- *Fertile flowers.*—Diameter: About 5 mm. Depth: About 4 mm. Shape: Rotate, campanulate. Petals: Quantity: Five. Length: About 3 mm. Width: About 1 mm. Shape: Broadly ovate. Apex: Acute. Base: Fused. Margin: Entire. Texture, upper and lower surfaces: Smooth, glabrous. Color: When opening and fully opened, upper surface: Close to 71B to 71C. When opening and fully opened, lower surface: Close to 72D. Sepals: Quantity: Five. Length: About 3 mm. Width: About 1.5 mm. Shape: Ovate. Apex: Acute. Base: Fused. Margin: Entire. Texture, upper and lower surfaces: Smooth, glabrous. Color: When opening, upper and lower surfaces: Close to 145B to 145C. Fully opened, upper and lower surfaces: Close to 145B; towards the margins flushed with close to 69B to 69C. Pedicels: Length: About 4 mm. Diameter: About 1 mm. Strength: Moderately strong. Angle: About 10° from vertical. Texture: Smooth, glabrous. Color: Between 67D and 68B. Reproductive organs: Stamens: Quantity per flower: About ten. Filament length: About 2 mm. Filament color: Close to 155C. Anther shape: Broadly reniform. Anther length: About 0.8 mm. Anther color: Close to 197C to 197D. Pollen amount: Scarce. Pollen color: Close to 156D. Pistils: Pistil quantity per flower: About three. Pistil length: About 2 mm. Stigma shape: Club-shaped. Stigma color: Close to N155A. Style length: About 1.5 mm. Style color: Close to N155A. Ovary color: Close to N155C.
- *Sterile flowers.*—Petals: None observed. Sepals: Quantity: Four. Length: About 1.2 cm. Width: About 1.1 cm. Shape: Orbicular to broadly deltoid. Apex: Rounded to bluntly acute. Base: Cuneate. Margin: Entire. Texture, upper and lower surfaces: Smooth, glabrous. Color: When opening, upper surface: Close to 64C. When opening, lower surface: Close to 73B.

Fully opened, upper surface: Close to 70C tinged with close to between 144B and 145A. Fully opened, lower surface: Close to 70D tinged with close to 145B to 145C. Pedicels: Length: About 2.2 cm. Diameter: About 1.5 mm. Strength: Moderately strong. Angle: About 35° from vertical. Texture: Smooth, glabrous. Color: Close to 67B to 67C. Reproductive organs: None observed. Fruits/seeds: Fruit and seed development have not been observed on plants of the new *Hydrangea*.

Disease/pest resistance: Plants of the new *Hydrangea* have not been observed to be resistant to pathogens or pests common to *Hydrangea*.

Temperature tolerance: Plants of the new *Hydrangea* have been shown to be tolerant to temperatures ranging from about −20° C. to about 40° C.

It is claimed:

1. A new and distinct *Hydrangea* plant named 'Hokomac' as illustrated and described.

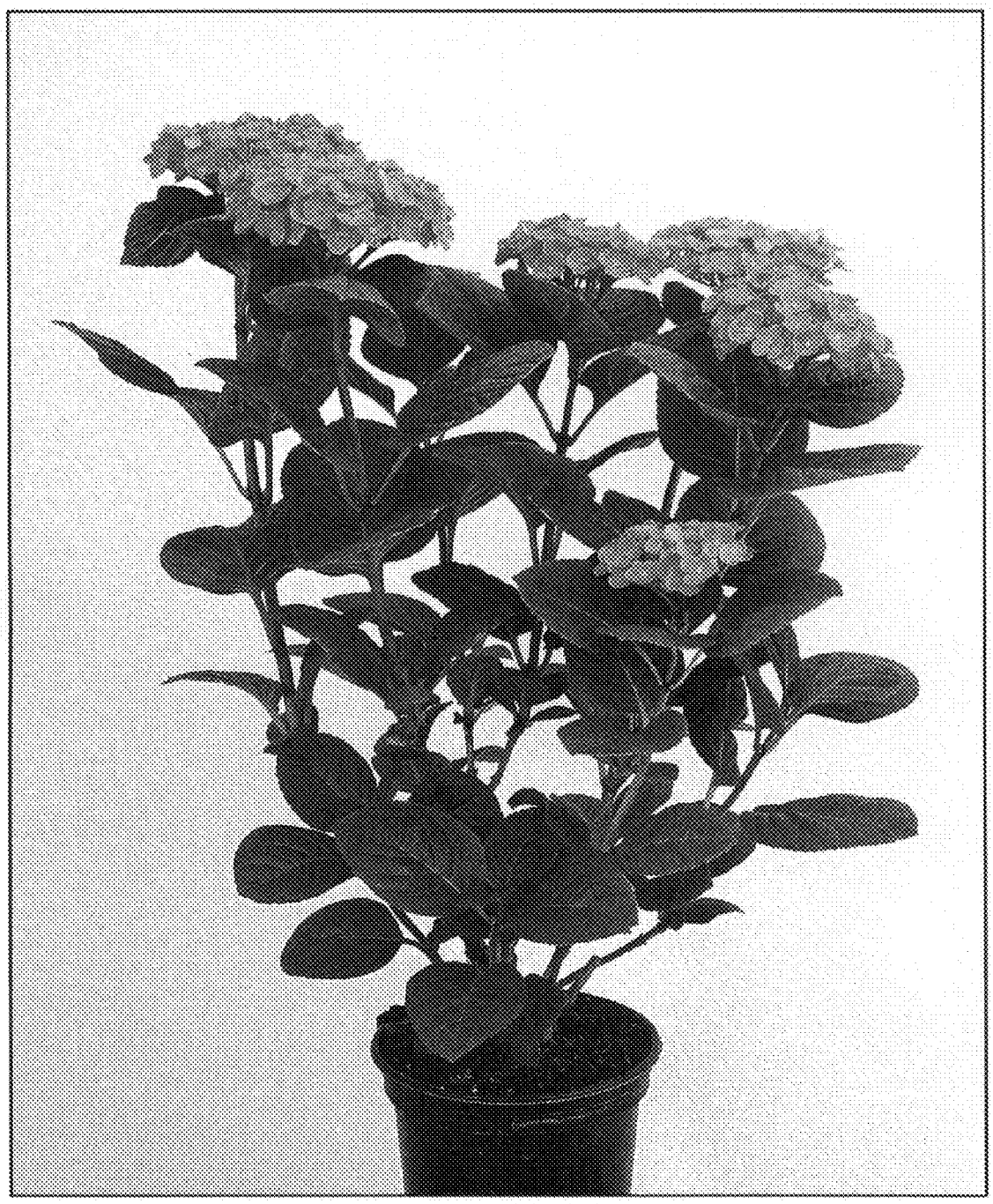

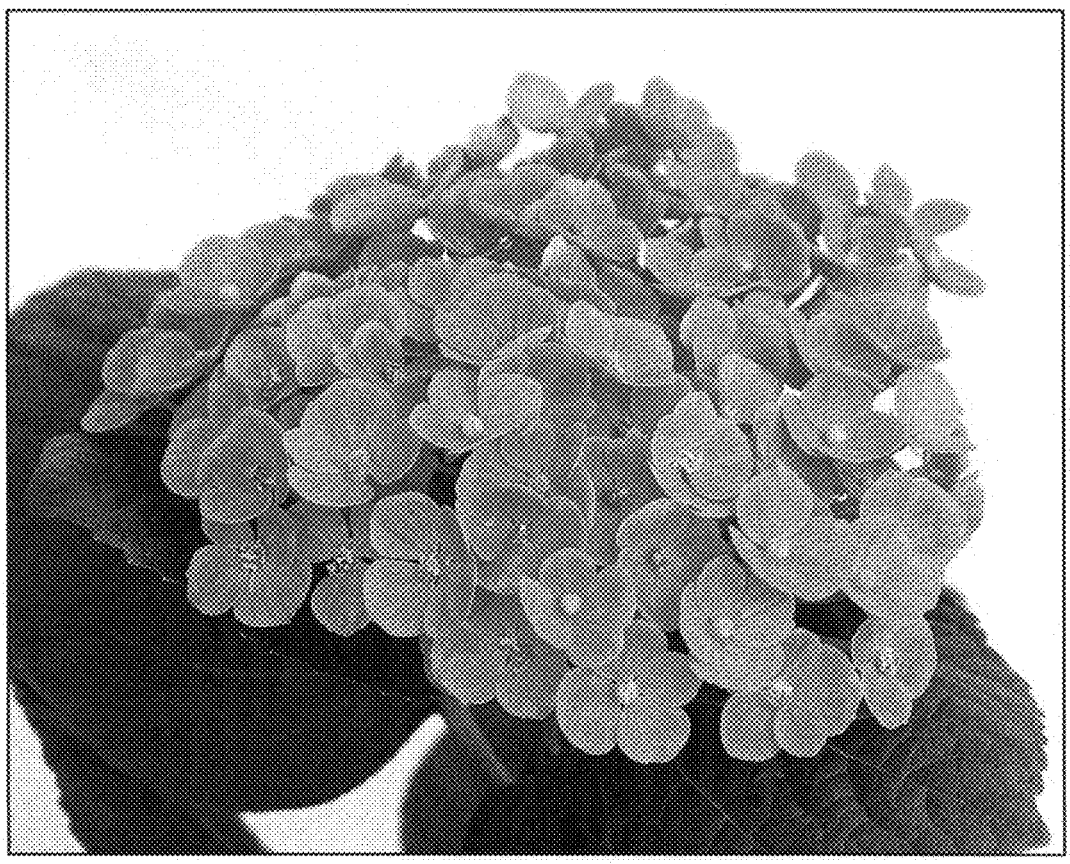
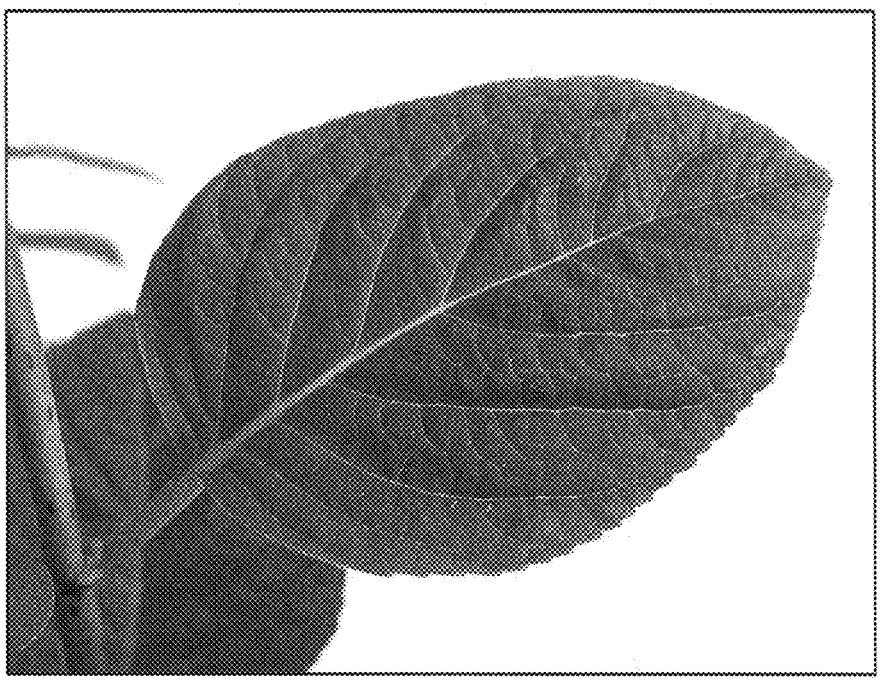

* * * * *